(12) United States Patent
Pavani (10) Patent No.: US 10,027,928 B2
(45) Date of Patent: Jul. 17, 2018

(54) MULTIPLE CAMERA COMPUTATIONAL WAFER INSPECTION

(71) Applicant: Sri Rama Prasanna Pavani, Palo Alto, CA (US)

(72) Inventor: Sri Rama Prasanna Pavani, Palo Alto, CA (US)

(73) Assignee: Exnodes Inc., Fremont, CA (US)

( * ) Notice: Subject to any disclaimer, the term of this patent is extended or adjusted under 35 U.S.C. 154(b) by 235 days.

(21) Appl. No.: 14/526,484

(22) Filed: Oct. 28, 2014

(65) Prior Publication Data
US 2016/0116419 A1 Apr. 28, 2016

(51) Int. Cl.
*H04N 7/18* (2006.01)
*G01N 21/95* (2006.01)

(52) U.S. Cl.
CPC ......... *H04N 7/181* (2013.01); *G01N 21/9501* (2013.01)

(58) Field of Classification Search
CPC ........... G01N 21/8806; G01N 21/9501; G01N 2201/06113; H04N 7/181
USPC .......................................................... 348/87
See application file for complete search history.

(56) References Cited

U.S. PATENT DOCUMENTS

| | | | |
|---|---|---|---|
| 5,754,226 A * | 5/1998 | Yamada | G06T 3/4007 348/155 |
| 5,768,443 A * | 6/1998 | Michael | G06T 7/002 382/151 |
| 5,822,055 A | 10/1998 | Tsai et al. | |
| 5,859,698 A | 1/1999 | Chau et al. | |
| 6,628,390 B1 * | 9/2003 | Johnson | G01B 11/26 356/400 |
| 6,864,971 B2 | 3/2005 | Lin et al. | |
| 7,916,180 B2 * | 3/2011 | Olsen | H01L 27/14645 348/218.1 |
| 9,418,435 B2 * | 8/2016 | Hayashi | G06T 7/593 |
| 2004/0012775 A1 * | 1/2004 | Kinney | G01N 21/9501 356/237.2 |
| 2005/0225632 A1 * | 10/2005 | Iffland | G01N 21/956 348/87 |
| 2008/0304055 A1 * | 12/2008 | Oshima | G01N 21/9501 356/237.5 |
| 2009/0087079 A1 * | 4/2009 | Onoda | G06K 9/00 382/141 |
| 2010/0060895 A1 * | 3/2010 | Oshima | G01N 21/47 356/369 |

(Continued)

*Primary Examiner* — Jeremaiah C Hallenbeck-Huber
*Assistant Examiner* — Boubacar Abdou Tchoussou (57) ABSTRACT

A system and method for inspecting a surface, comprising: illuminating said surface with an electromagnetic radiation to generate scattered radiation, having a plurality of scattering angles, from features of said surface; collecting said scattered radiation from said surface at two or more positions, with radiation collected at each position forming an image of a plurality of points on said surface by collecting a portion of said scattered radiation propagating in a subset of said scattering angles; detecting images of surface at two or more said positions; and combining information from two or more said images of surface to generate a global information set, having information from a plurality of said scattering angles collected by two or more said imaging modules, whereby said features of said surface are detected in said images of surface and in said global information set.

20 Claims, 8 Drawing Sheets

(56) References Cited

U.S. PATENT DOCUMENTS

| | | | |
|---|---|---|---|
| 2010/0183197 A1* | 7/2010 | Aikawa | G01B 11/026 382/106 |
| 2010/0328435 A1* | 12/2010 | Puah | G01B 11/0608 348/47 |
| 2011/0085050 A1* | 4/2011 | Dowski, Jr. | G02B 27/0075 348/222.1 |
| 2012/0019813 A1* | 1/2012 | Yoshitake | G01M 11/0207 356/213 |

* cited by examiner

MULTIPLE CAMERA COMPUTATIONAL WAFER INSPECTION

FIELD OF THE INVENTION

This invention relates generally to wafer inspection and more particularly to multiple camera wafer inspection having a wide field of view and a large numerical aperture.

BACKGROUND

Wafer inspection systems are widely used in semiconductor integrated circuit (IC) fabrication to inspect semiconductor wafers for the presence of abnormalities or defects. IC fabrication involves an extensive process comprising of hundreds of process steps such as implantation, deposition, lithography, etching, and polishing. Knowing with certainty that a process step was performed within tolerable limits of excursion is important to maximize production yield. Yield is defined as the ratio of the number of ICs that meet target specifications to the total number of ICs produced. Functional performance tests on ICs are often possible only after the completion of fabrication of ICs. Meanwhile, a problem in a particular process step may propagate to multiple wafers leading to a serious impact on production yield. To mitigate the possibility of having such a serious impact on yield, it is desirable to inspect semiconductor wafers after every significant step in IC fabrication.

Semiconductor fabs maximize production yield by first establishing maximum tolerable defect count after each significant process step. This is followed by continual monitoring of defect count during production using wafer inspection tools. When defect count exceeds predetermined maximum tolerable limits, information about the properties of defects on wafer, such as size and shape, are obtained from optical and electron based wafer inspection tools. The defect properties thus obtained are used to identify and eliminate the root cause of the defects. For example, consider that defect properties point to the occurrence of a particular type of defect (say, type A). With this information, semiconductor fabs proceed to identify suspicious process steps that are likely to produce defect type A. Each suspicious process step may then be closely examined to identify and eliminate the root-cause(s) of defect type A. Information about defects encountered after each significant process step may also be passed on to future process steps so that future process steps could optimize their recipes to account for existing defects. By promptly detecting excursions in defect count and bringing them back to normalcy, the risk of propagation of defects to a large number of wafers can be contained. Mitigating such a risk leads to yield maximization.

In the last few decades, semiconductor ICs have continually improved in performance. Remarkably, they have also become increasingly inexpensive over the same time period. This trend of performance improvement at lower cost has been primarily made possible by two factors: a) technology node shrinking, and b) wafer size expansion. Technology node shrinking refers to the trend of decreasing sizes of components inside an IC. This leads to a reduction of the size of an IC die, and consequently to an increase in the number of ICs fabricated per wafer. Wafer size expansion refers to the trend of increasing diameters of semiconductor wafers. An increase in wafer size for a given die size also results in an increase in the number of ICs fabricated per wafer. By being able to produce increasingly more ICs per wafer, advances in semiconductor fabrication have been able to not only improve performance but also reduce cost.

However, achieving and maintaining high production yield is becoming increasingly challenging with advanced semiconductor fabrication technologies. This is because defect sensitivity of wafer inspection tools have been significantly lagging behind technology node scaling. Over the last decade, while semiconductor technology nodes shrank from 130 nm to 14 nm (over 9× reduction), defect sensitivity of wafer inspection tools improved from 50 nm to 20 nm (2.5× reduction). In other words, semiconductor technology nodes have been shrinking 3.7 times faster than defect sensitivity. This trend is concerning because maximizing yield of ICs is dependent on minimizing defects that are as small as the smallest structures in ICs. Due to the slower rate of improvement in defect sensitivity of wafer inspection tools, an increasing number of yield affecting defects pass through undetected in leading-edge semiconductor fabrication, resulting in a significant reduction in production yield.

Traditional dark-field wafer inspection tools scan a tiny spot (few micrometers wide) of a laser beam through as many as a billion different points to inspect the entire surface of a large (hundreds of millimeters wide) leading-edge semiconductor wafer. Scattered radiation from the spot is collected with a collection optic having a large numerical aperture and a small field of view. Due to the elaborate scanning procedure, traditional wafer inspection tools are inherently slow. This leads to a reduction in the number of wafers that can be inspected in an hour, a metric known as inspection throughput. In an attempt to improve throughput, these tools scan the spot at high speeds by rapidly moving the wafer. However, any increase in throughput obtained by speeding up scanning comes at the price of reduced defect sensitivity. This is because the amount of time the spot spends on a defect decreases with an increase in scanning speed, leading to a reduction in scattered energy from the defect.

Traditional wafer inspection tools suffer from a number of problems: a) reduced defect sensitivity; b) reduced inspection throughput; c) negligible defect recognition capability; d) trade-off between defect sensitivity and inspection throughput; e) reduced field-of view; f) trade-off between field of view and numerical aperture; g) decreased reliability due to high-speed scanning; and h) deformation of wafer due to high-speed scanning.

Accordingly, there is a need for an improved wafer inspection system that can improve defect sensitivity; improve inspection throughput; improve defect recognition capabilities; relax trade-off between defect sensitivity and inspection throughput; increase field of view; relax trade-off between field of view and numerical aperture; improve reliability; and eliminate wafer deformation.

SUMMARY

The invention is a system and method for multiple camera wafer inspection having a wide field of view and a large numerical aperture.

In some embodiments, the invention is a system for inspecting a surface, comprising: an electromagnetic radiation incident on said surface to generate scattered radiation, having a plurality of scattering angles, from features of said surface; two or more imaging modules positioned to collect said scattered radiation from said surface, with each imaging module forming an image of a plurality of points on said surface by collecting a portion of said scattered radiation propagating in a subset of said scattering angles; two or more image sensors positioned to detect images of surface formed by said imaging modules; and a processor configured to combine information from two or more said images of surface to generate a global information set, having information from a plurality of said scattering angles collected by two or more said imaging modules, whereby said features of said surface are detected in said images of surface and in said global information set.

In some embodiments, the invention is a method for inspecting a surface, comprising: illuminating said surface with an electromagnetic radiation to generate scattered radiation, having a plurality of scattering angles, from features of said surface; collecting said scattered radiation from said surface at two or more positions, with radiation collected at each position forming an image of a plurality of points on said surface by collecting a portion of said scattered radiation propagating in a subset of said scattering angles; detecting images of surface at two or more said positions; and combining information from two or more said images of surface to generate a global information set, having information from a plurality of said scattering angles collected by two or more said imaging modules, whereby said features of said surface are detected in said images of surface and in said global information set.

DETAILED DESCRIPTION OF THE PREFERRED EMBODIMENTS

Figure 1:
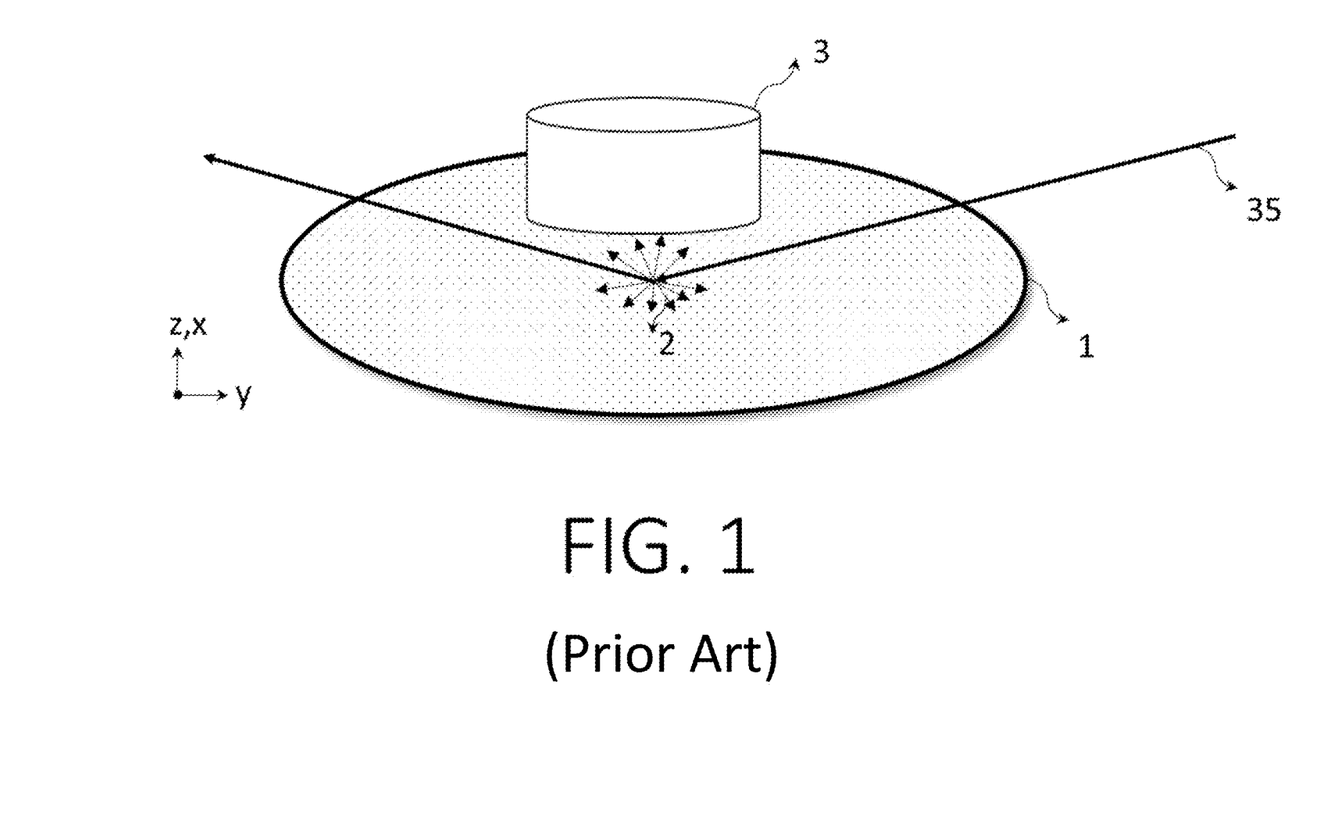
FIG. 1 shows a traditional wafer inspection system, according to prior art.

FIG. 1 shows a traditional wafer inspection system, according to prior art. In a traditional system, a laser beam 35 is incident on surface 1. The laser beam 35 illuminates a spot on the surface. Upon incidence on surface 1, the beam 35 undergoes specular reflection from smooth regions of the surface. When a defect is present under the spot illuminated by the beam, scattered radiation 2 is generated by the defect. The number of photons in scattered radiation 2 is a small fraction of incident photons. Typically, not more than a few photons in a million incident photons are scattered. The number of scattered photons depends on the properties of the defect, such as size, shape, and material properties. The scattered photons are collected by a collection optic 3 having a large numerical aperture and a narrow field of view. The large numerical aperture helps in collecting scattered light from a wide range of polar and azimuthal angles. The field of view of collection optic 3 is often matched to the spot size of incident illumination. The scattered radiation collected by collection optic 3 is focused on a photodetector that generates an electrical output. The electrical output is analyzed to determine the presence or absence of a defect under the spot. For example, if the electrical output at a spot is similar to the electrical output at neighboring spots, then it is determined that a defect is not present under the spot. On the other hand, if the electrical output at a spot is substantially different from the electrical output at neighboring spots, then it is determined that a defect is present under the spot.

In the traditional wafer inspection system of FIG. 1, the size of spot is typically a few micrometers and the size of the wafer can be as large as hundreds of millimeters. In order to inspect the entire area of surface 1, the spot is scanned across as many as a billion points sequentially. Consequently, traditional dark field wafer inspection tools are inherently slow, and suffer from low inspection throughput. In an attempt to increase throughput of inspection, these traditional tools rapidly move the wafer relative to the spot. While high speed scanning may increase inspection throughput, it unfortunately also has a detrimental impact on defect sensitivity. This is because defect sensitivity is related to the total amount of scattered energy detected from a defect. As the speed of scanning is increases, the amount of time an illumination spot spends on a defect decreases. Consequently, the total energy scattered by the defect decreases, leading to a reduction in defect sensitivity.

The large numerical aperture required to collect scattered radiation from a wide range of polar and azimuthal angles makes it impractical for collection optic 3 to have a large field of view. As a result, the traditional wafer inspection system of FIG. 1 suffers from a limited field of view.

Traditional wafer inspection tools have a number of disadvantages: a) reduced defect sensitivity due to high-scanning speed; b) reduced inspection throughput due to sequential scanning of extremely large number of points; c) negligible defect recognition capability due to limited number of photodetectors; d) trade-off between defect sensitivity and inspection throughput because of the tight dependence on defect sensitivity on scanning speed; e) reduced field-of view due to the requirement to have a large numerical aperture; f) trade-off between field of view and numerical aperture; g) decreased reliability due to the presence of components moving at high speed; and h) deformation of wafer due to air currents created by high-speed scanning.

Figure 2:
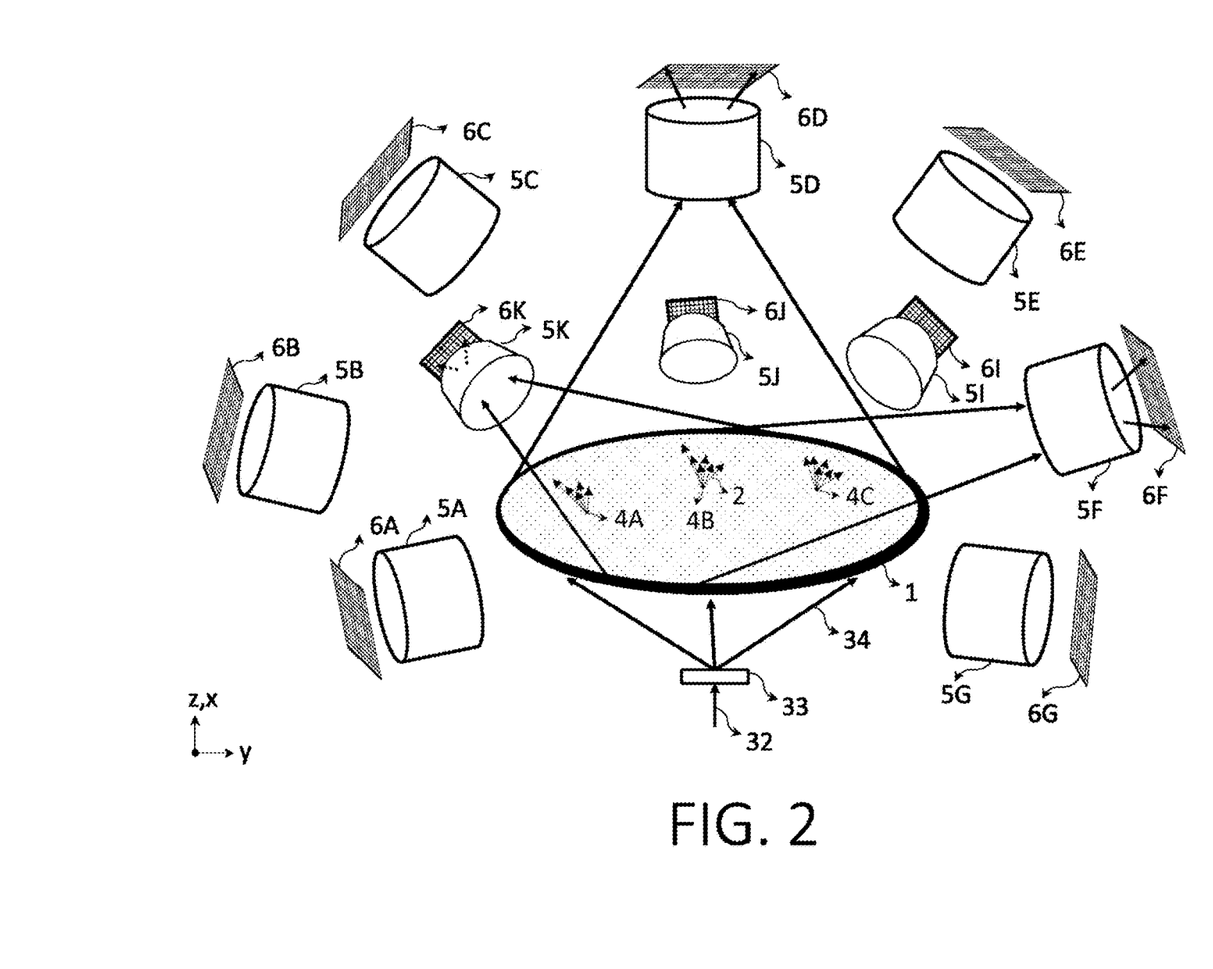
FIG. 2 illustrates a multiple camera wafer inspection system, in accordance with the invention.

FIG. 2 illustrates a multiple camera wafer inspection system, in accordance with the invention. An electromagnetic beam 32 is incident on a beam expander 33 to generate an expanded beam 34. The expanded beam 34 illuminates a large area of a surface 1. Surface 1 typically has both smooth regions and non-smooth regions. Smooth regions are featureless regions of surface 1. Features of a surface refer to any deviation, abnormality, or a defect whose shape is unlike its local neighborhood. Non-smooth regions of surface are regions with such features. The expanded electromagnetic radiation 34 is incident both on smooth and non-smooth regions of surface 1. The radiation incident on smooth regions undergoes specular reflection. The angle of specular reflection of radiation is identical to the angle of incidence of the radiation on surface 1. In non-smooth regions of surface 1, the incident electromagnetic radiation is scattered by features, such as defects. Three defects 4A, 4B, and 4C are present on surface 1. All three defects scatter the incident electromagnetic radiation. Defect 4B generates scattered radiation 2. The radiation from defects scatter in a wide range of polar and azimuthal angles. Multiple imaging modules, 5A, 5B, 5C, 5D, 5E, 5F, 5G, 5I, 5J, and 5K, are positioned to collect scattered radiation from defects. The field of view of each imaging module covers a substantial area of surface 1. In some embodiments, the field of view of each imaging module covers the entire area of surface 1. The imaging modules collect scattered radiation propagating at different polar and azimuthal angles. The scattered radiation collected by imaging modules, 5A, 5B, 5C, 5D, 5E, 5F, 5G, 5I, 5J, and 5K, are focused on image sensors, 6A, 6B, 6C, 6D, 6E, 6F, 6G, 6I, 6J, and 6K, respectively. The image sensors capture images of surface 1 from different points of view. The image sensors may be of complementary metal oxide semiconductor (CMOS) type or charge coupled device (CCD) type. The image of surface detected by each image sensor cover a substantial area of said surface. In some embodiments, each image of surface covers the entire area of surface 1. The images captured by image sensors are combined to generate one or more global information sets of surface 1. A global information set has information from a plurality of scattering angles collected by two or more imaging modules. In some embodiments, combining information from two or more images of surface comprises: transforming two or more images of surface to generate two or more global images of surface having a global coordinate system; registering two or more global images of surface to generate two or more registered images of surface; and integrating two or more registered images of surface to generate a global information set. Defect positions on surface 1 are detected from one or more global information sets and images captured from image sensors. Defect pixel regions are extracted from the neighborhood of detected defect positions. The defect pixel regions are further processed to estimate the properties of defects such as size, shape, and material composition. In other embodiments, combining information from two or more images of surface comprises: estimating local defect properties from each image of surface; transforming local defect properties from two or more images of surface to generate transformed local defect properties having a global coordinate system; and integrating transformed local defect properties.

In some embodiments, imaging modules are positioned at predetermined locations so that a substantial amount of scattered radiation from a first feature type is incident on an imaging module A and a substantial amount of scattered radiation from a second feature type is not incident on imaging module A. In some embodiments, imaging modules are positioned at predetermined locations so that a substantial amount of scattered radiation from a feature type F is incident on an imaging module A and a substantial amount of scattered radiation from the feature type F is not incident on an imaging module B. In some embodiments, properties of features present on surface 1 are estimated using steps comprising: generating a first global information set of surface by combining two or more images of surface; generating a second global information set of surface by combining two or more images of surface, wherein at least one image of surface that is used for generating second global information set is not used for generating first global information set; and comparing first global information set with second global information set. Defects may be classified into different defect types by comparing the first and second global information sets. For example, consider a defect type A that scatters along a first set of scattering angles, but not along a second set of scattering angles. Further, consider a defect type B that scatters along a both first and second sets of scattering angles. In this example, the first set of scattering angles correspond to the first global information set, and the second set of scattering angles correspond to the second global information set. Accordingly, defect type A would be detected in the first global information set but not in the second global information set. However, defect type B would be detected in both first and second global information sets. Thus, defect A may be classified from defect B by comparing the first and second global information sets.

The position of imaging modules and their respective image sensors can be changed according to properties of defects and the properties of surface 1. In some embodiments, the imaging modules are positioned to maximize scattering intensities from features, such as defects, from surface 1. In other embodiments, imaging modules are positioned to minimize scattering intensities from smooth featureless background regions. Smooth featureless background regions refer to surface roughness of surface 1. The standard deviation of surface roughness is typically much smaller than the size of yield-affecting defects. Nevertheless, they are present throughout the area of surface 1, unlike defects that are relatively more localized. As a result, surface roughness generates a non-negligible scattered radiation that is also detected by image sensors. This scattered radiation caused by surface roughness is called as haze. Haze is detected by image sensors together with scattered radiation from defects. Haze has the potential to overwhelm signal from tiny defects. Accordingly, it is desirable to minimize haze. In some embodiments, imaging modules are positioned to maximize collection of scattered radiation from defects, but minimize collection of scattered radiation from surface roughness (haze). In some embodiments, imaging modules are positioned to maximize signal to background ratio of signal from defects. Signal to background refers to the ratio of detected signal from scattered radiation from a defect to the detected signal from surface roughness or haze. The scattering intensity profile of scattered radiation from a defect depends on the properties of defect such as its size, shape, and material composition. Scattering intensity profile refers to the intensity of scattered radiation in different polar and azimuthal scattering angles. Scattering intensity profiles vary widely according to different defect properties. Prior information about scattering intensity profiles of defects may be used to position imaging modules so that they maximize collection of scattered radiation from defects. Prior information about scattering intensity profiles of defects may be obtained from methods such as experimental calibration of scattering intensity profile of defects and computational modeling of scattering from defects. Similarly, the scattering intensity profile of surface depends surface properties such as roughness profile and material composition. Prior information about scattering intensity profile of surface may be used to position imaging modules in order to minimize collection of scattered radiation from surface roughness. Prior information about scattering intensity profiles of surface may be obtained from methods such as experimental calibration of scattering intensity profile of surface and computational modeling of scattering from surface. A recipe comprising a desired position values for imaging modules may also be followed for positioning imaging modules.

A combination comprising of an imaging module and an image sensor, which detects radiation focused by the imaging module, is referred to as a camera. Accordingly, the wafer inspection system of FIG. 2 comprises multiple cameras. In some embodiments, the position of each camera can be controlled in a number of ways, including: translation along x dimension, translation along y dimension, translation along z dimension, rotation about x dimension, rotation about y dimension, and rotation about z dimension. In other embodiments, one group of cameras have fixed positions and rotational orientations, while another group of cameras have variable positions and rotational orientations. In some embodiments, imaging modules comprise zoom systems. In some embodiments, zoom values of imaging modules may be modified according to the three-dimensional positions and three-dimensional orientations of imaging modules. In some embodiments, imaging modules comprise amplitude and phase filters that modulate scattered radiation collected by the imaging modules. The wafer inspection system of FIG. 2 comprises means for positioning imaging modules at locations that are prescribed by an inspection recipe. In some embodiments, cameras are attached to arched rails that allows the cameras to be moved along the surface of the rails. In other embodiments, cameras are attached to robotic arms to achieve translation and rotation.

In some embodiments, imaging modules are scanned so that plurality of scattering angles are collected. In other embodiments, the surface is tilted so that plurality of scattering angles are collected by imaging modules. In general, collecting a wide range of scattering angles increases detection of radiation from both defects and surface roughness. In some embodiments, such a scan may be useful for generating a profile of surface roughness. In other embodiments, such a scan may be useful for detecting defects that have a very wide range of scattering angles.

In some embodiments, electromagnetic beam 32 has a wavelength that maximizes reflected power from surface. The reflection coefficient of surface 1 is dependent on the refractive index of surface 1, and the refractive index of surface 1 exhibits a dependence on wavelength of beam 32. Therefore, the wavelength of the electromagnetic beam 32 can be designed to maximize refractive index, and consequently maximize reflected power. Reflected power coefficient is calculated as the square of reflection coefficient. In some embodiments, the wavelength of beam 32 is designed to maximize the difference in refractive index between surface 1 and the medium in which beam 32 propagates immediately before illuminating surface 1. Maximizing this difference in refractive index increases reflected power and scattered intensity from defects. The intensity of scattered light from a defect is inversely proportional to the fourth power of wavelength. Lower wavelengths are therefore more desirable to maximize the intensity scattered radiation. In some embodiments, the wavelength of electromagnetic radiation is chosen as the smallest wavelength that maximizes the refractive index of surface 1. In other embodiments, the wavelength of electromagnetic radiation is chosen as the wavelength at which the intensity of scattered radiation from a defect located on surface 1 is maximized. In some embodiments, electromagnetic beam 32 has a wavelength that maximizes quantum efficiency of the image sensors. An image sensor comprises a plurality of photodetectors called as pixels. The quantum efficiency of a photodetector is the ratio of the number of photoelectrons detected by the photodetector to the number of photons incident on the photodetector. Quantum efficiency of a photodetector exhibits a dependence on wavelength of electromagnetic radiation incident on it. The sensitivity of the photodetector, defined as the smallest detectable number of photons, and the signal to noise ratio of the photodetector can be maximized by choosing a wavelength that maximizes the quantum efficiency of the photodetectors. Maximizing the quantum efficiency of photodetectors present in image sensors improves the quality of images detected by image sensors. In some embodiments, electromagnetic beam 32 has a polarization that maximizes reflected power from surface. In some embodiments, an s-polarization (perpendicular to the plane of incidence) is used for beam 32 to maximize reflected power from surface 1. S-polarized radiation also maximizes scattered light from defects. In some embodiments, electromagnetic beam 32 has an angle of incidence that maximizes reflected power from surface. Angle of incidence refers to the angle beam 34 makes with the normal of surface 1. The reflection coefficient of surface 1 increases as the angle of incidence of a beam increases.

Figure 3:
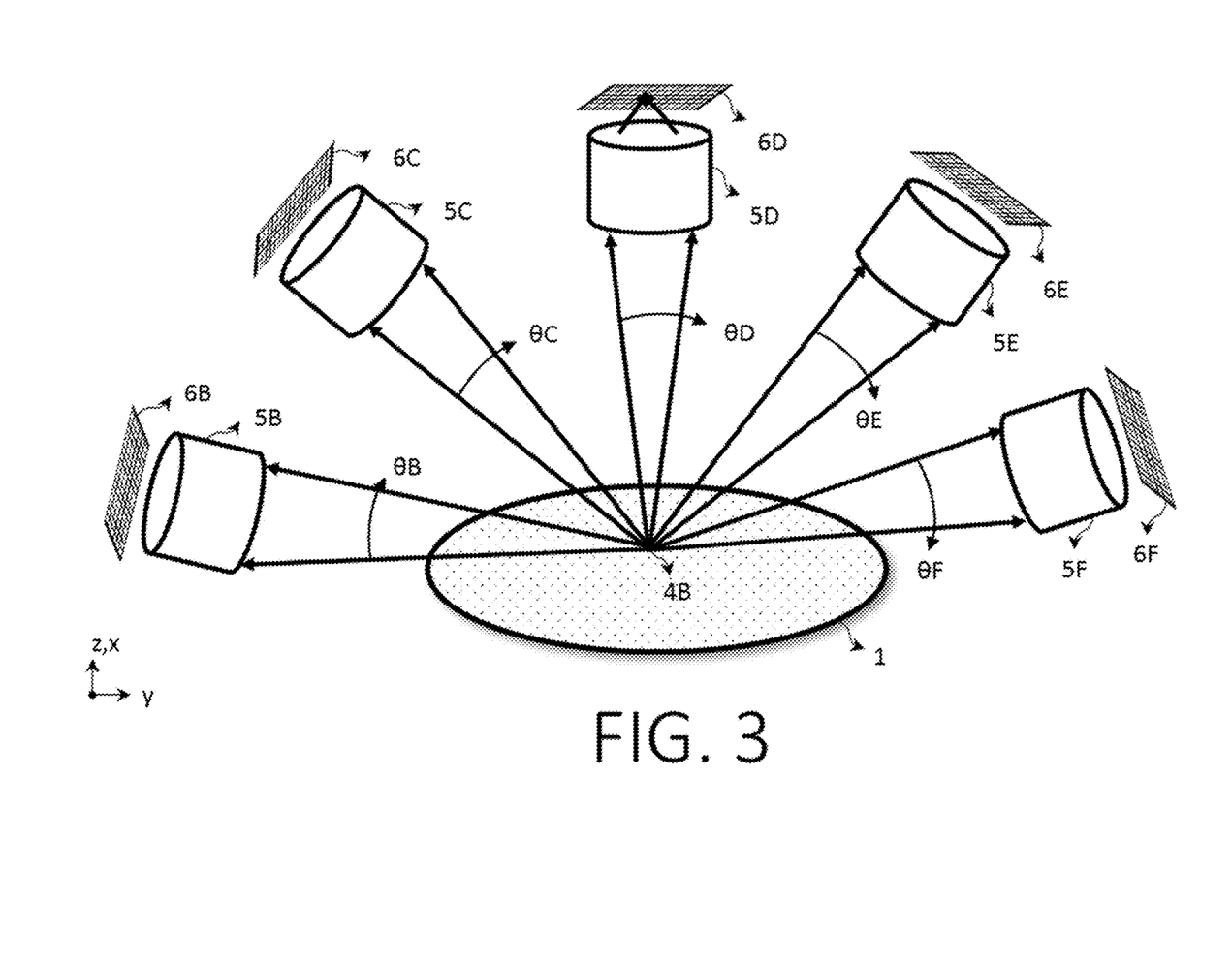
FIG. 3 shows a portion of a multiple camera wafer inspection system with four cameras, in accordance with the invention.

FIG. 3 shows a portion of a multiple camera wafer inspection system with four cameras, in accordance with the invention. A defect 4B present on surface 1 scatters electromagnetic radiation in a wide range of angles. Imaging modules, 5B, 5C, 5D, 5E, and 5F, collect scattered radiation from defect 4B. The scattered radiation collected by imaging modules, 5B, 5C, 5D, 5E, and 5F, are focused on image sensors 6B, 6C, 6D, 6E, and 6F, respectively. The imaging modules image a substantial area of surface 1 on the image sensors. In some embodiments, the entire area of surface 1 is imaged by imaging modules on image sensors. Accordingly, the imaging modules have a large field of view. In some embodiments, the numerical aperture of an imaging module is smaller than the angular range of scattered radiation from defects. However, since each of the imaging modules, 5B, 5C, 5D, 5E, and 5F, captures a different subset of scattering angles from defect 4B. A combination of numerical apertures from all imaging modules spans a substantial range of scattering angles of defect 4B. Imaging modules, 5B, 5C, 5D, 5E, and 5F, have cone angles of $\theta_B$, $\theta_C$, $\theta_D$, $\theta_E$, and $\theta_F$, respectively. In some embodiments, cameras comprising imaging modules and image sensors, are positioned to maximize collection and detection of scattered radiation from defects, and minimize collection and detection of scattered radiation from surface roughness.

Figure 4:
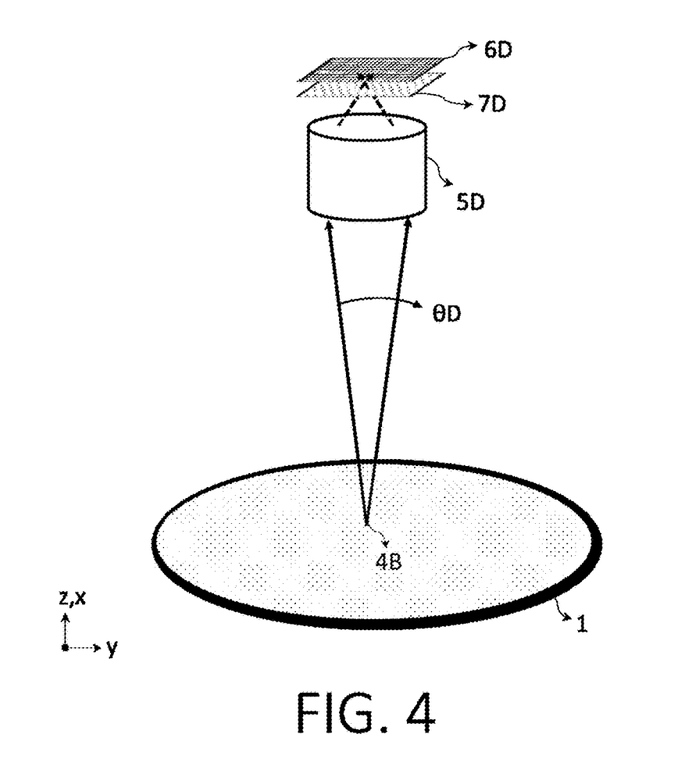
FIG. 4 depicts a camera with an integrated micro-optic sensor layer, in accordance with the invention.

FIG. 4 depicts a camera with an integrated micro-optic sensor layer 7D, in accordance with the invention. In some embodiments, image sensors comprise a micro-optic sensor layer 7D to detect phase of said scattered radiation. A surface 1 comprising a defect 4B scatters electromagnetic radiation in a wide range of scattering angles. A portion of the scattered radiation is collected by imaging module 5D. The imaging module 5D has a cone angle of $\theta_D$. The scattered radiation collected by imaging module 5D is focused on a micro-optic sensor layer 7D. The radiation from micro-optic sensor layer 7D is detected by an image sensor 6D. The micro-optic sensor layer is used for detecting phase of scattered radiation. The micro-optic sensor layer 7D comprises a plurality of lenses implemented as a refractive optical element or a diffractive optical element. In some embodiments, each lens of the micro-optic sensor layer generates an image of the aperture of the imaging optic 5D on the pixels of image sensor 6D. A finite number of pixels are allocated in image sensor 6D for each lens on the micro-optic sensor layer 7D. The pixels allocated for a lens of micro-optic sensor layer 7D are located around the center of the optical axis of the lens. From the intensities of pixels allocated for the lens, the phase gradient of scattered radiation incident on the lens is determined. For example, if the pixel intensity corresponds to a focused spot in the center of the allocated pixels (on the optical axis of lens), then the scattered radiation can be estimated to have a zero phase gradient when it is incident on the surface of the lens. Alternatively, if the pixel intensity corresponds to a focused spot that is not at the center of the allocated pixels for the lens, then the scattered light can be estimated to have a linear phase gradient that is proportional to the distance between the focused spot and the center of allocated pixels. Accordingly, a phase gradient value can be estimated for each lens of the micro-optic sensor layer 7D. A phase gradient profile for the surface of the micro-optic sensor layer 7D can be estimated by combining phase gradients of a plurality of lenses in the micro-optic sensor layer 7D using a stitching algorithm. The phase profile of scattered radiation, P(x,y), is computed from the estimated phase gradient profile by calculating a two dimensional integration of the phase gradient profile. The intensity of scattered light, I(x,y), is obtained from the pixel intensities detected by image sensor 6D. The electromagnetic field of scattered light, C(x,y), is calculated from the intensity and phase of scattered radiation as, $C(x,y) = \sqrt{I(x,y)} e^{(-iP(x,y))}$. The electromagnetic field C(x,y) may then be propagated using computational propagation to bring different planes in focus. For example, C(x,y) may be computationally propagated to bring surface 1 in focus. Alternatively, C(x,y) may be propagated to bring a plane above or below surface 1 in focus, thereby generating a defocused image of surface 1.

In some embodiments, computational propagation is performed in the spatial frequency domain by first computing spatial frequencies of electromagnetic field using a transformation. Then, a propagation transfer function is computed and multiplied with spatial frequencies of the electromagnetic field. In some embodiments, computing spatial frequencies of an electromagnetic field involves the calculation of $\tilde{C}(k_x, k_y) = F\{C(x,y)\}$, where C(x,y) is electromagnetic field, F refers to Fourier transform, and $\tilde{C}(k_x, k_y)$ is the spatial frequency of C(x,y). Propagation transfer function, $\tilde{H}(k_x, k_y)$, is computed as $$\tilde{H}(k_x, k_y) = e^{\left(i\Delta z \sqrt{(k^2 - k_x^2 - k_y^2)}\right)},$$

where $k = 2\pi n/\lambda$, n is refractive index, $\lambda$ is the wavelength of the electromagnetic beam, and $\Delta z$ is the distance through which the electromagnetic field is propagated. The electromagnetic field after propagation is computed as, $F^{-1}\{\tilde{C}(k_x, k_y)\tilde{H}(k_x, k_y)\}$, where $F^{-1}$ refers to inverse Fourier transformation. In other embodiments, computational propagation of an electromagnetic field is performed by first computing an impulse response or point spread function of propagation, and then computing a convolution of the electromagnetic field with the impulse response. The impulse response of propagation is calculated as $$F^{-1}\left\{e^{\left(i\Delta z \sqrt{(k^2 - k_x^2 - k_y^2)}\right)}\right\}.$$

In some embodiments, $\Delta z$ is calculated as the product of the square of the magnification of imaging module 5D with the distance in z through which the field needs to be propagated in the object space (near surface 1). In some embodiments, computational propagation may be achieved by using digital refocusing algorithms that operate in the geometrical optics regime by rearranging pixel values to compute different focal planes.

In some embodiments, the image is captured with a micro-optic sensor layer to facilitate phase detection. In other embodiments, image is captured without a micro-optic sensor layer. In some embodiments, at least two images are captured with at least two different optical path lengths between imaging optic and image sensor. Phase is then estimated by using the transport of intensity equation. In some embodiments, the optical path length between an imaging module and an image sensor can be varied so that said scattered radiation is detected at multiple values of optical path length. In some embodiments, optical path length between imaging optic and image sensor may be varied by using a liquid crystal layer. In other embodiments, optical path length between image sensor and imaging optic may be varied by inserting a uniform phase plate, such as a glass plate, between imaging optic and image sensor. In some embodiments, optical path length between the image sensor and the imaging optic may be varied by changing the distance between imaging optic and image sensor using an actuator. In some embodiments, an iterative optimization algorithm may be used to estimate phase profile by starting with a random initial estimate for phase and arriving at a final estimate by propagating the electromagnetic field between two or more image planes separated by the optical path length.

Figure 5:
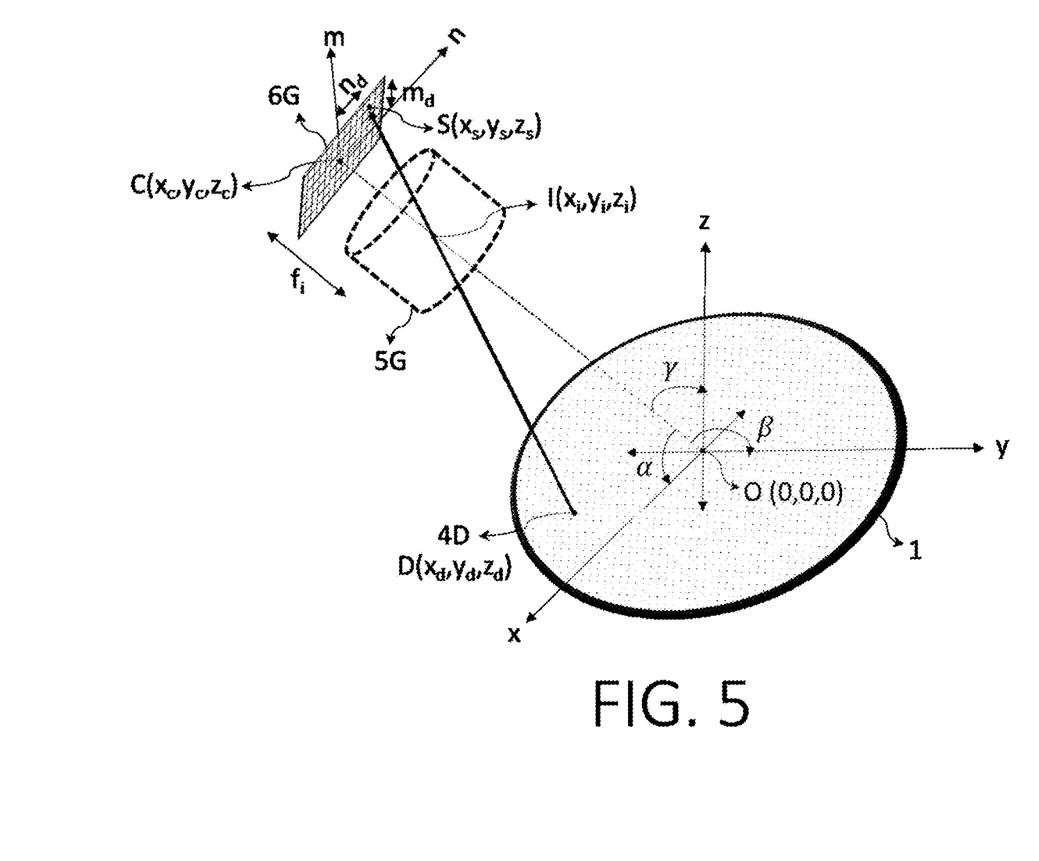
FIG. 5 shows camera parameters used to estimate the position of a defect, in accordance with the invention.

FIG. 5 shows camera parameters used to estimate the position of a defect 4D on surface 1, in accordance with the invention. Scattered radiation from defect 4D is incident on imaging module 5G and is detected by image sensor 6G. The origin of the x-y-z coordinate system O (x=0, y=0, z=0) is at the center of surface 1. The optical center of imaging module 5G is at point I having the coordinate I ($x_i$, $y_i$, $z_i$). Further, the optical axis of imaging module 5G passes through point I and is oriented at an angle ($\alpha, \beta, \gamma$) with respective to positive x, y, and z axes, respectively. An image sensor 6G is located on a plane normal to the optical axis of imaging module 5G, separated by a distance $f_i$ (along the optical axis) from point I. The point at which the optical axis intersects the image sensor is the origin of image sensor C($x_c$, $y_c$, $z_c$). Pixels of image sensor 6G are oriented along m-n axes. The chief ray, a ray propagating from defect 4D through the optical center I of imaging module 5G, is incident on image sensor 6G at a distance ($m_d$, $n_d$) from the origin C of image sensor. In the x-y-z coordinate system, the coordinates of the point of intersection of the chief ray and the image sensor is denoted as S($x_s$, $y_s$, $z_s$). Furthermore, x-y-z coordinates of the defect 4D is denoted as D($x_d$, $y_d$, $z_d$). A point in the coordinate system of image sensor (m-n axes) can be transformed into the x-y-z coordinate system of the surface 1 using the steps described below. That is, the following procedure describes the steps to determine ($x_d$, $y_d$, $z_d$) from ($m_d$, $n_d$). In some embodiments, the image coordinates of a defect ($m_d$, $n_d$) is estimated by localizing the position of the intensity of the image of defect using a centroid estimator, a peak estimator, Gaussian fitting, or by fitting with a model of the point spread function of the imaging module 5G. In some embodiments, every point of the image captured by image sensor 6G is transformed into the x-y-z coordinate system. The center position I($x_i$, $y_i$, $z_i$) and orientation ($\alpha, \beta, \gamma$) of imaging module 5G are known, are therefore considered as prior information. The procedure to determine D($x_d$, $y_d$, $z_d$) involves the determination of C($x_c$, $y_c$, $z_c$) and S($x_s$, $y_s$, $z_s$). This is followed by the use of S($x_s$, $y_s$, $z_s$) along with I ($x_i$, $y_i$, $z_i$) to form a three dimensional equation for the chief ray. D($x_d$, $y_d$, $z_d$) is finally determined by finding the point at which the three dimensional chief ray line intersects the plane of surface 1. The equation for the plane of surface 1 is z=0. The x-y-z coordinates of C($x_c$, $y_c$, $z_c$) are calculated as $x_c = x_i + f_i \cos(\alpha)$; $y_c = y_i + f_i \cos(\beta)$; and $z_c = z_i + f_i \cos(\gamma)$. The x-y-z coordinates of S($x_s$, $y_s$, $z_s$) are calculated as, $$\begin{bmatrix} x_s \\ y_s \\ z_s \end{bmatrix} = \left( R_z(\theta_z) R_y(\theta_y) R_x(\theta_x) \begin{bmatrix} -n_d \\ m_d \\ 0 \end{bmatrix} + \begin{bmatrix} x_c \\ y_c \\ z_c \end{bmatrix} \right),$$

where $\theta_x = (\gamma - \beta)$, $\theta_y = (\gamma - \alpha)$, $\theta_z = 90 - (\beta - \alpha)$, $$R_x(\theta_x) = \begin{bmatrix} 1 & 0 & 0 \\ 0 & \cos(\theta_x) & -\sin(\theta_x) \\ 0 & \sin(\theta_x) & \cos(\theta_x) \end{bmatrix},$$

$$R_y(\theta_y) = \begin{bmatrix} \cos(\theta_y) & 0 & \sin(\theta_y) \\ 0 & 1 & 0 \\ -\sin(\theta_y) & 0 & \cos(\theta_y) \end{bmatrix}, \text{ and}$$

$$R_z(\theta_z) = \begin{bmatrix} \cos(\theta_z) & -\sin(\theta_z) & 0 \\ \sin(\theta_z) & \cos(\theta_z) & 0 \\ 0 & 0 & 1 \end{bmatrix}.$$

Finally, the x-y-z coordinates of $D(x_d, y_d, z_d)$ are calculated as $x_d = x_s - ([z_s(x_i - x_s)]/(z_i - z_s))$; $y_d = y_s - ([z_s(y_i - y_s)]/(z_i - z_s))$; $z_d = 0$.

Figure 6:
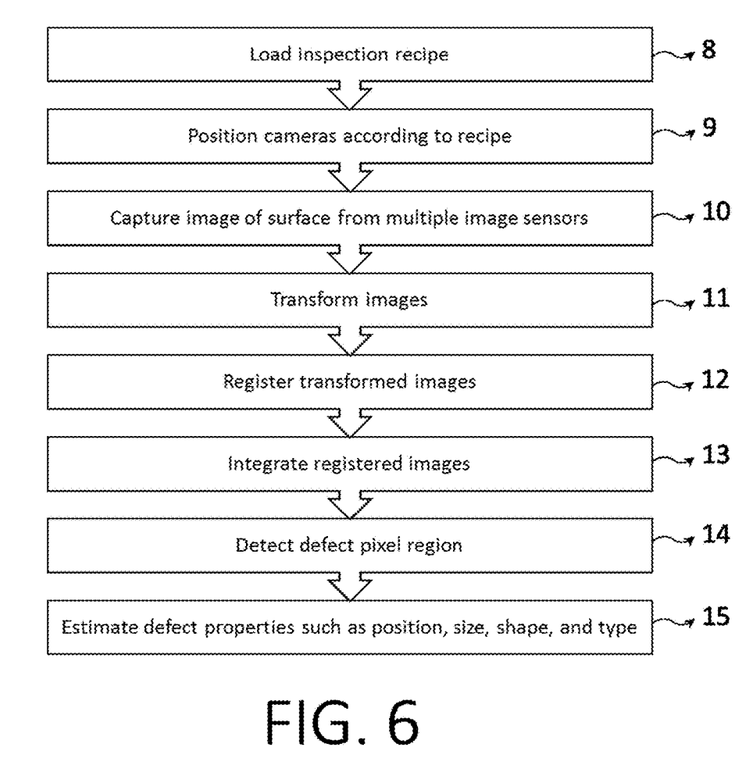
FIG. 6 shows an exemplary flow chart describing steps for estimating properties of defects on a surface using a combine-estimate procedure, in accordance with the invention.

FIG. 6 shows an exemplary flow chart describing steps for estimating properties of defects on a surface using a combine-estimate procedure, in accordance with the invention. In block 8, an inspection recipe is loaded by a processor in the multiple camera wafer inspection system. The inspection recipe comprises position information and imaging parameters for multiple cameras. The position information of cameras are predetermined based on the type of defects that are of interest to the wafer inspection system. For example, if the inspection system is primarily interested in detecting particulate defects, then the cameras are positioned to maximize collection of scattered radiation of particles. Alternatively, if the inspection system is primarily interested in detecting process induced defects, then the cameras are positioned to maximize collection of scattered radiation from process induced defects. In these examples, scattering intensity profiles of particles and defects are used as prior information to determine optimal position of cameras. The scattering intensity profiles of different defect types may be obtained by experimental calibration or by using computational scattering models. In some embodiments, the positions of cameras may be determined to maximize collection of scattered radiation from multiple defect types. In these cases, scattering intensity profiles from multiple defect types are integrated together to determine the optimal positions of cameras. In some embodiments, it may be desirable to not only detect defects but also recognize defect properties such as shape. In these cases, cameras may be positioned to distinguish scattered radiation from two or more defect types. For example, a first camera could be positioned at a scattering angle at which a first defect shape scatters significantly while a second defect shape does not scatter significantly. Further, a second camera could be positioned at a scattering angle where both the first and second defect shapes scatter significantly. In such a configuration, the presence of two defects can be verified from an image acquired from the second camera, and the classification of the two defect types can be performed from an image acquired from the first camera. In block 9, cameras are positioned as specified in the recipe. Positioning a camera includes setting the three-dimensional positions and three-dimensional rotation angles of the camera. In some embodiments, a subset of cameras are fixed in predetermined positions and orientations. In some embodiments, a subset of cameras can be repositioned or reoriented as specified in the recipe. Cameras may be repositioned or reoriented using robotic arms. Cameras may also be repositioned or reoriented by attaching them to rails that allow motion of cameras along a predetermined track established by the rail. Furthermore, cameras could be repositioned or reoriented by connecting them to two orthogonally running cables and by pulling or releasing the cables to achieve arbitrary positions and orientations. Pan and tilt mechanical modules having stepper motors could also be used to reorient cameras. In block 10, images are detected by multiple image sensors. The settings of image sensors, such as gain and exposure time, may be specified in the recipe. Images are captured from image sensors. In some embodiments, a micro-optic sensor layer is positioned between an imaging module and an image sensor to detect phase of scattered radiation, in addition to the intensity of scattered radiation. In some embodiments, the detected images are converted into intensity and phase components to generate the complex electromagnetic field of scattered radiation. The electromagnetic field may be propagated to generate a focused or a defocused image of the surface. In block 11, the images captured from image sensors are transformed into global images by transforming them into a global coordinate system. Each captured image from an image sensor represents an image of surface with a unique perspective projection. In some embodiments, each point $(m_d, n_d)$ on the image sensor plane is transformed into x-y coordinates as $x_d = x_s - ([z_s(x_i - x_s)]/(z_i - z_s))$; $y_d = y_s - ([z_s(y_i - y_s)]/(z_i - z_s))$, where $$\begin{bmatrix} x_s \\ y_s \\ z_s \end{bmatrix} = \left( R_z(\theta_z) R_y(\theta_y) R_x(\theta_x) \begin{bmatrix} -n_d \\ m_d \\ 0 \end{bmatrix} + \begin{bmatrix} x_c \\ y_c \\ z_c \end{bmatrix} \right),$$

$\theta_x = (\gamma - \beta)$, $\theta_y = (\gamma - \alpha)$, $\theta_z = 90 - (\beta - \alpha)$, $x_c = x_i + f_i \cos(\alpha)$, $y_c = y_i + f_i \cos(\beta)$, $$z_c = z_i + f_i \cos(\gamma), R_x(\theta_x) = \begin{bmatrix} 1 & 0 & 0 \\ 0 & \cos(\theta_x) & -\sin(\theta_x) \\ 0 & \sin(\theta_x) & \cos(\theta_x) \end{bmatrix},$$

$$R_y(\theta_y) = \begin{bmatrix} \cos(\theta_y) & 0 & \sin(\theta_y) \\ 0 & 1 & 0 \\ -\sin(\theta_y) & 0 & \cos(\theta_y) \end{bmatrix}, \text{ and}$$

$$R_z(\theta_z) = \begin{bmatrix} \cos(\theta_z) & -\sin(\theta_z) & 0 \\ \sin(\theta_z) & \cos(\theta_z) & 0 \\ 0 & 0 & 1 \end{bmatrix}.$$

In block 12, the transformed images from multiple image sensors are registered or aligned with each other with sub-pixel precision in x and y dimensions. The purpose of alignment is to ensure that identical features on different images line up to have identical x and y coordinates. In some embodiments, alignment is performed by up-sampling (interpolating) individual images from two image sensors, shifting the first image with respect to the second image in x and y dimensions, subtracting pixel regions having a similar feature in both images, and positioning the first image at the shift position that minimizes the sum of subtracted pixel values in the feature region. In block 13, the registered images are integrated to form one or more global information sets of surface. In some embodiments, a global information set is formed by adding pixel values of the registered images. In other embodiments, a global information set is formed by averaging pixel values of registered images. In some embodiments, multiple global information sets are computed by adding or averaging pixels from different combinations of registered images.

In block 14, one or more images of surface, including transformed images of surface and global information sets of surface, are processed to separate defect pixels from background pixels. In some embodiments, a focused global information set of surface or a focused transformed image of surface is used for detecting defect pixels. This is because of the presence of high intensity values of defect pixels in focused global information sets and focused transformed images of surface. Defect pixels may be classified from their background pixels using an intensity threshold value. To minimize false positives, threshold values are designed to be higher than background pixel values. The value of a threshold may be adaptively chosen depending on pixel intensities in local neighborhood. For example, threshold value in a region with high background is higher than the threshold value in a region with lower background. In some embodiments, a focused defect may be modeled and the model shape may be correlated with image of surface. Such a correlation operation creates correlation peaks at the position of defects. Correlation peaks may then be distinguished from their background using an intensity threshold value. For each defect, a defect pixel region, comprising a predetermined number of pixels that are surrounding the detected defect pixels, is segmented for estimating defect properties.

In block 15, a defect pixel region is processed to estimate defect properties such as position on wafer, size, shape, and type. Multiple images of surface, including focused global information set of surface, defocused global information set of surface, and transformed image of surface, may be used for estimating defect properties. The position of a defect on a surface may be accurately estimated by comparing a model of defect with the defect pixel region. For example, error values between model and measured defect pixels is computed for a variety of position values. The position value with least error is estimated as the position of defect on surface. In some embodiments, the position of a defect may also be estimated from peak, centroid, or midpoint of the defect pixel region. The size of defect may be calculated by measuring the width of the defect along one, two, or three dimensions from multiple global information sets and transformed images of surface. Size of defect may refer to length, area, or volume of a defect. The shape of a defect may be obtained from defect pixel regions in multiple global information sets and transformed images of surface. In some embodiments, a defocused image of a surface or a defocused global information set may comprise more information about the shape of defect than their focused counterparts. This is because scattered radiation from defect is detected by more number of pixels in a defocused images of surface and defocused global information sets. A defocused global information set refers to a global information set generated by combining defocused images of surface. A focused global information set refers to a global information set generated by combining focused images of surface. The defect pixels may be fitted with models of focused and defocused defect profiles. Comparisons may include comparisons of both pixel intensity and pixel phase. Models of defects include scaled, rotated, translated, and other deformed versions of numerous known defect types such as particles, process induced defects, ellipsoids, crystal originated pits (COP), bumps, scratches, and residues. In some embodiments, an error metric is computed by calculating the difference between defect pixels and model pixels. The model with minimum error value may be declared as an estimate of defect type.

Figure 7:
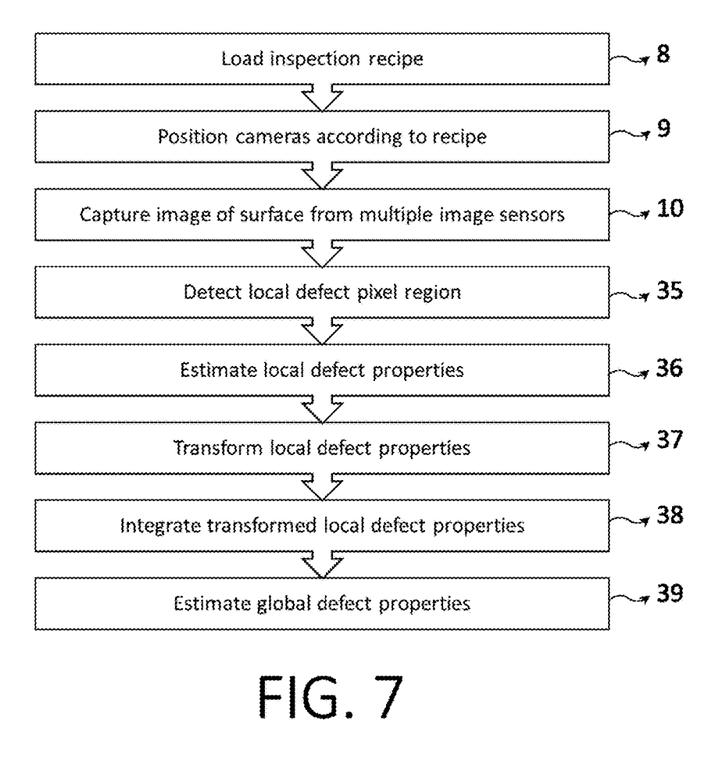
FIG. 7 shows an exemplary flow chart describing steps for estimating properties of defects on a surface using an estimate-combine procedure, in accordance with the invention.

FIG. 7 shows an exemplary flow chart describing steps for estimating properties of defects on a surface using an estimate-combine procedure, in accordance with the invention. In block 8, an inspection recipe is loaded by a processor in the multiple camera wafer inspection system. The inspection recipe comprises position information and imaging parameters for multiple cameras. The position information of cameras are predetermined based on the type of defects the wafer inspection system is most interested in. For example, if the inspection system is primarily interested in detecting particulate defects, then the cameras are be positioned to maximize collection of scattered radiation of particles. Alternatively, if the inspection system is primarily interested in detecting process induced defects, then the cameras are positioned to maximize collection of scattered radiation from process induced defects. In these examples, scattering intensity profiles of particles and defects are used as prior information to determine optimal position of cameras. The scattering intensity profiles of different defect types may be obtained by experimental calibration or by using computational scattering models. In some embodiments, the positions of cameras may be determined to maximize collection of scattered radiation from multiple defect types. In these cases, scattering intensity profiles from multiple defect types are integrated together to determine the optimal positions of cameras. In some embodiments, it may be desirable to not only detect defects but also recognize defect properties such as shape. In these cases, cameras may be positioned to distinguish scattered radiation from two or more defect types. For example, a first camera could be positioned at a scattering angle at which a first defect shape scatters significantly while a second defect shape does not scatter significantly. Further, a second camera could be positioned at a scattering angle where both the first and second defect shapes scatter significantly. In such a configuration, the presence of two defects can be verified from an image acquired from the second camera, and the classification of the two defect types can be performed from an image acquired from the first camera. In block 9, cameras are positioned as specified in the recipe. Positioning a camera involves setting its three-dimensional positions and three-dimensional rotation angles. In some embodiments, a subset of cameras are fixed in predetermined positions and orientations. In some embodiments, a subset of cameras can be repositioned or reoriented as specified in the recipe. Cameras may be repositioned or reoriented using robotic arms. Cameras may also be repositioned or reoriented by attaching them to rails that allow motion of cameras along a predetermined track established by the rail. Furthermore, cameras could be repositioned or reoriented by connecting them to two orthogonally running cables and by pulling or releasing the cables to achieve arbitrary positions and orientations. A pan and tilt mechanical module having stepper motors could also be used to reorient cameras. In block 10, images are detected by multiple image sensors. The settings of image sensors, such as gain and exposure time, may be specified in the recipe. Images are captured from image sensors. In some embodiments, a micro-optic sensor layer is positioned between an imaging module and an image sensor to detect phase of scattered radiation, in addition to the intensity of scattered radiation. In some embodiments, the detected images are converted into intensity and phase components to generate the complex electromagnetic field of scattered radiation. The electromagnetic field may be propagated to generate a focused or a defocused image of the surface under inspection.

In block 35, one or more images captured from each image sensor are processed separately to separate local defect pixels from background pixels. In some embodiments, a focused image of surface is used for detecting defect pixels. This is because of the presence of high intensity values of defect pixels in focused images. In a focused image of a surface, defect pixels may be classified from their background pixels using an intensity threshold value. To minimize false positives, threshold values are designed to be higher than background pixel values. The value of a threshold may be adaptively chosen depending on pixel intensities in local neighborhood. For example, threshold value in a region with high background is higher than the threshold value in a region with lower background. In some embodiments, a focused defect may be modeled and the model shape may be correlated with image of surface. Such a correlation operation creates correlation peaks at the position of defects. Correlation peaks may then be distinguished from their background using an intensity threshold value. For each defect, a defect pixel region, comprising a predetermined number of pixels that are surrounding the detected defect pixels, is segmented for estimating defect properties.

In block 36, local defect pixel regions from each image sensor is processed separately to estimate defect properties such as position on wafer, size, shape, and type. Multiple images of surface, including focused and defocused images of surface, may be used for estimating defect properties. The position of a defect on a surface may be accurately estimated by comparing a model of defect with the defect pixel region. For example, error values between model and measured defect pixels is computed for a variety of position values. The position value with least error is estimated as the position of defect on surface. In some embodiments, the position of a defect may also be estimated from peak, centroid, or midpoint of the defect pixel region. The size of defect may be calculated by measuring the width of the defect along one, two, or three dimensions from multiple focused and defocused global information sets of surface. Size of defect may refer to length, area, or volume of a defect. The shape of a defect may be obtained from defect pixel regions in multiple focused and defocused images of surface. In some embodiments, a defocused image of a surface may comprise more information about the shape of defect than a focused image. This is because scattered radiation from defect is detected by more number of pixels in a defocused image than in a focused image. The defect pixels may be fitted with models of focused and defocused defect profiles. Comparisons may include comparisons of both pixel intensity and pixel phase. Models of defects include scaled, rotated, translated, and other deformed versions of numerous known defect types such as particles, process induced defects, ellipsoids, crystal originated pits (COP), bumps, scratches, and residues. In some embodiments, an error metric is computed by calculating the difference between defect pixels and model pixels. The model with minimum error value may be declared as an estimate of defect type.

In block 37, properties of defects, such as position and shape, estimated from each image sensor are transformed into global properties by transforming them into a global coordinate system. The positions or shapes of defects estimated from each image sensor represents a unique perspective projection of the positions or shapes of defect on surface. In some embodiments, each position point $(m_d, n_d)$ on the image sensor is transformed into x-y coordinates as
$x_d = x_s - ([z_s(x_i - x_s)]/(z_i - z_s))$; $y_d = y_s - ([z_s(y_i - y_s)]/(z_i - z_s))$, where $$\begin{bmatrix} x_s \\ y_s \\ z_s \end{bmatrix} = \left( R_z(\theta_z) R_y(\theta_y) R_x(\theta_x) \begin{bmatrix} -n_d \\ m_d \\ 0 \end{bmatrix} + \begin{bmatrix} x_c \\ y_c \\ z_c \end{bmatrix} \right),$$

$\theta_x = (\gamma - \beta)$, $\theta_y = (\gamma - \alpha)$, $\theta_z = 90 - (\beta - \alpha)$, $x_c = x_i + f_i \cos(\alpha)$, $y_c = y_i + f_i \cos(\beta)$, $z_c = z_i + f_i \cos(\gamma)$, $$R_x(\theta_x) = \begin{bmatrix} 1 & 0 & 0 \\ 0 & \cos(\theta_x) & -\sin(\theta_x) \\ 0 & \sin(\theta_x) & \cos(\theta_x) \end{bmatrix},$$

$$R_y(\theta_y) = \begin{bmatrix} \cos(\theta_y) & 0 & \sin(\theta_y) \\ 0 & 1 & 0 \\ -\sin(\theta_y) & 0 & \cos(\theta_y) \end{bmatrix}, \text{ and}$$

$$R_z(\theta_z) = \begin{bmatrix} \cos(\theta_z) & -\sin(\theta_z) & 0 \\ \sin(\theta_z) & \cos(\theta_z) & 0 \\ 0 & 0 & 1 \end{bmatrix}.$$

In block 38, the transformed position or shape information from multiple image sensors are integrated to form a global estimate for position or shape. In some embodiments, global estimate for position or shape is computed by averaging transformed position or transformed shape estimates obtained from individual image sensors. In other embodiments, global estimate for position or shape is computed as a weighted average of transformed position or transformed shape estimates obtained from individual image sensors. A weight may be assigned to a given estimate based on the quality of the estimate. For example, an estimate with higher precision (low noise) is given a higher weight than an estimate with lower precision (high noise).

Figure 8:
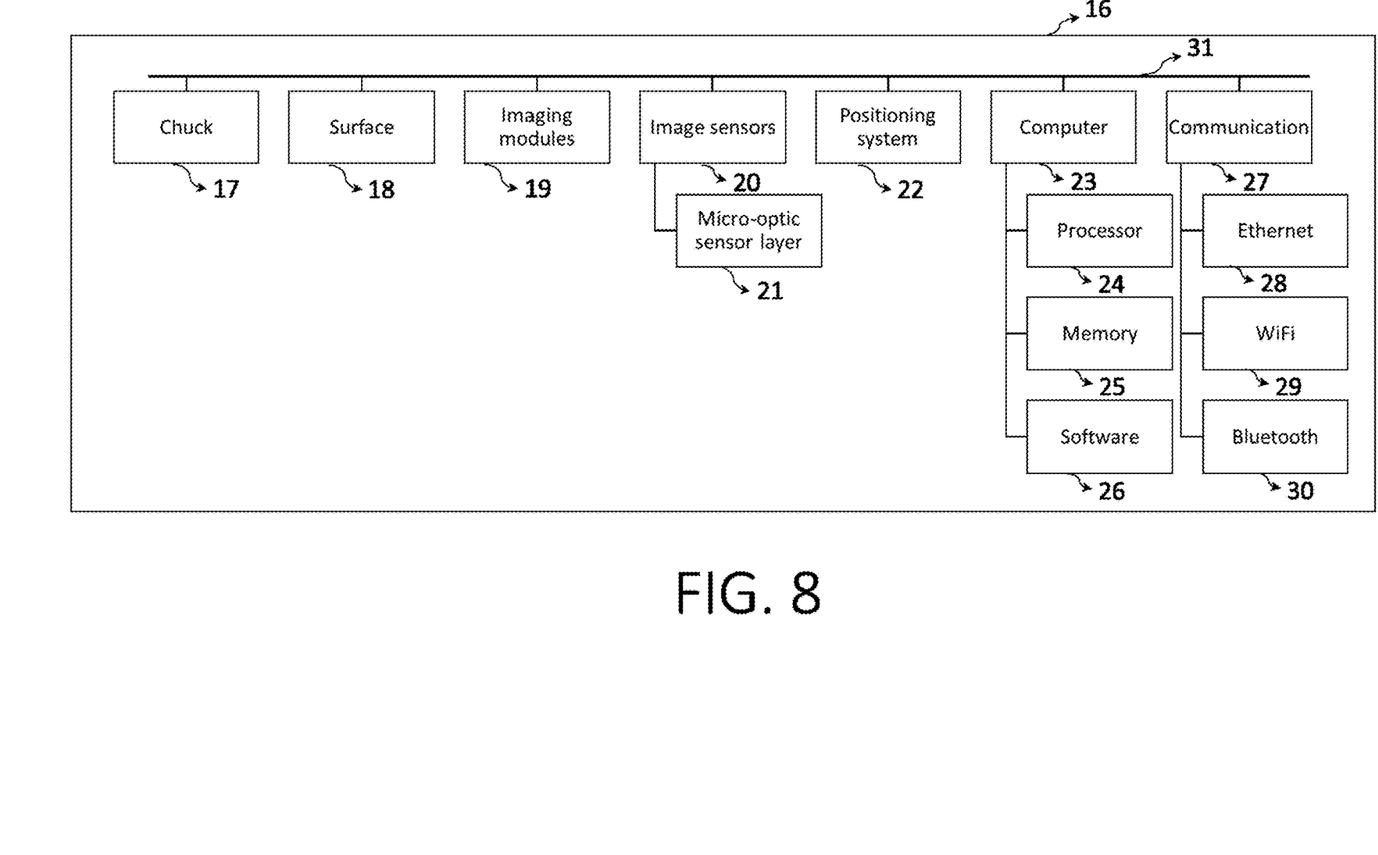
FIG. 8 illustrates a block diagram of a multiple camera wafer inspection system, in accordance with the invention.

FIG. 8 illustrates a block diagram of a multiple camera wafer inspection system, in accordance with the invention. A bus 31 connects various blocks of system 16, namely chuck 17, surface 18, illumination, imaging modules 19, image sensors 20, positioning system 22, computer 23, and communication 27. Data and control signals are carried by bus 31. Chuck 17 includes an edge handling system that holds the edge of surface, vacuum system that holds the back side of surface with vacuum suction, gas vents, and support structures used to hold surface 18 flat. Surface 18 comprises the region to be inspected by system 16. Surface 18 may be flat, curved due to gravity induced sag, or deformed due to coatings. Illumination includes laser beams and beam expanders. Imaging modules 19 comprise multiple imaging optics that form images of surface 18 by detecting subset of scattered radiation propagating at different angles. Image sensors 20 capture scattered radiation from surface and transfers image data through bus 31 to computer 23. In some embodiments, Image sensors 20 may include a micro-optic sensor layer 21 to facilitate phase detection. Image sensors 20 receive control information to adjust parameters such as exposure time and gain from computer through bus 31. Computer 23 includes a processor 24, memory 25, and software 26. Software 26 processes image data from image sensors 20 to compute a number of entities, including: intensity and phase profiles of electromagnetic field; computational propagation to compute image of scattered radiation; transformation from image plane to surface plane; defect pixel region; defect properties such as position, size, shape, and type. Software 26 generates control information and sends them through bus 31 to chuck 17, surface 18, illumination, imaging modules 19, and image sensors 20. Computer 23 connects to communication block 27 for communicating data and control information through bus 31. Communication block 31 includes Ethernet 28, WiFi 29, and Bluetooth 30.

It will be recognized by those skilled in the art that various modifications may be made to the illustrated and other embodiments of the invention described above, without departing from the broad inventive scope thereof. It will be understood therefore that the invention is not limited to the particular embodiments or arrangements disclosed, but is rather intended to cover any changes, adaptations or modifications which are within the scope and spirit of the invention as defined by the appended claims.

It should be understood that the present invention as described above can be implemented in the form of control logic using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described above, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

In the claims, reference to an element in the singular is not intended to mean "one and only one" unless explicitly stated, but rather is meant to mean "one or more." In addition, it is not necessary for a device or method to address every problem that is solvable by different embodiments of the invention in order to be encompassed by the claims.

The above description is illustrative and is not restrictive. Many variations of the disclosure will become apparent to those skilled in the art upon review of the disclosure. The scope of the disclosure should, therefore, be determined not with reference to the above description, but instead should be determined with reference to the pending claims along with their full scope or equivalents.

One or more features from any embodiment may be combined with one or more features of any other embodiment without departing from the scope of the disclosure. Further, modifications, additions, or omissions may be made to any embodiment without departing from the scope of the disclosure. The components of any embodiment may be integrated or separated according to particular needs without departing from the scope of the disclosure.

What is claimed is:

1. A system for inspecting a surface, comprising:
    an electromagnetic radiation incident on a plurality of regions of said surface at the same time to generate scattered radiation, having a plurality of scattering angles, from features of said surface;
    two or more imaging modules positioned to collect said scattered radiation from said surface at the same time, with each imaging module forming a perspective image of at least a portion of said plurality of regions of said surface by collecting at least a portion of said scattered radiation propagating in a subset of said scattering angles, wherein said perspective image formed by each imaging module corresponds to the same region of said surface;
    two or more image sensors, having a two dimensional array of pixels, positioned to detect images of surface formed by said imaging modules at the same time; and
    a processor configured to
        estimate electromagnetic field of said scattered radiation by computing the phase of said scattered radiation from said images of surface;
        estimate computed images of surface by computationally propagating said electromagnetic field;
        estimate image pixel coordinates of a feature in a computed image of surface by localizing a pixel region of feature with a position estimator, wherein said pixel region of feature is a subset of said computed image of surface;
        compute position of said feature on said surface from said image pixel coordinates of feature by compensating for position, angular orientation and focal length of the imaging module corresponding to said computed image of surface;
        estimate type of said feature by comparing said pixel region of feature with a plurality of models of previously known feature types; and
        combine said position and type of feature from two or more said computed images of surface to generate a global information set, having information from a plurality of said scattering angles collected by two or more said imaging modules,
    whereby said features of said surface are detected, located, and classified in said global information set.

2. The system of claim 1, wherein said imaging modules are positioned at predetermined locations to maximize collection of scattered power from said features.

3. The system of claim 1, wherein said imaging modules are positioned at predetermined locations to minimize collection of scattered power from featureless regions of said surface.

4. The system of claim 1, wherein said imaging modules are positioned at predetermined locations so that a substantial amount of scattered radiation from a first feature type is incident on an imaging module A and a substantial amount of scattered radiation from a second feature type is not incident on said imaging module A.

5. The system of claim 1, wherein said imaging modules are positioned at predetermined locations so that a substantial amount of scattered radiation from a feature type is incident on an imaging module A and a substantial amount of scattered radiation from said feature type is not incident on an imaging module B.

6. The system of claim 1, further comprising means for positioning said imaging modules at locations that are prescribed by an inspection recipe.

7. The system of claim 1, wherein said computed images of surface cover a substantial area of said surface.

8. The system of claim 1, further comprising scanning of said imaging modules so that said plurality of scattering angles are collected.

9. The system of claim 1, further comprising tilting of said surface so that said plurality of scattering angles are collected by said imaging modules.

10. The system of claim 1, wherein said image sensors comprise micro-optic sensor layers to detect phase of said scattered radiation.

11. The system of claim 1, further comprising means for varying optical path length between said imaging modules and said image sensors so that said scattered radiation is detected at multiple values of optical path length.

12. The system of claim 1, wherein said electromagnetic radiation has a wavelength that maximizes reflected power from said surface.

13. The system of claim 1, wherein said electromagnetic radiation has a polarization that maximizes reflected power from said surface.

14. The system of claim 1, wherein said electromagnetic radiation has a wavelength that maximizes quantum efficiency of said image sensor.

15. The system of claim 1, wherein said electromagnetic radiation has an angle of incidence that maximizes reflected power from said surface.

16. A method for inspecting a surface, comprising:
illuminating a plurality of regions of said surface at the same time with an electromagnetic radiation to generate scattered radiation, having a plurality of scattering angles, from features of said surface;
collecting said scattered radiation from said surface at two or more positions at the same time, with radiation collected at each position forming a perspective image of at least a portion of said plurality of regions of said surface by collecting at least a portion of said scattered radiation propagating in a subset of said scattering angles, wherein said perspective image at each position corresponds to the same region of said surface;
detecting images of surface, having a two dimensional array of pixels, at two or more said positions at the same time;
estimating electromagnetic field of said scattered radiation by computing the phase of said scattered radiation from said images of surface;
estimating computed images of surface by computationally propagating said electromagnetic field;
estimating image pixel coordinates of a feature in a computed image of surface by localizing a pixel region of feature with a position estimator, wherein said pixel region of feature is a subset of said computed image of surface;
computing position of said feature on said surface from said image pixel coordinates of feature by compensating for position, angular orientation and focal length of the imaging module corresponding to said computed image of surface;
estimating type of said feature by comparing said pixel region of feature with a plurality of models of previously known feature types; and
combining said position and type of feature from two or more said computed images of surface to generate a global information set, having information from a plurality of said scattering angles collected by two or more said imaging modules,
whereby said features of said surface are detected, located, and classified in said global information set.

17. The method of claim 16, further comprising estimating the size of said feature from said pixel region of feature.

18. The method of claim 16, wherein said combining position and type of feature from two or more said computed images of surface comprises: transforming two or more said computed images of surface to generate two or more global images of surface having a global coordinate system; registering two or more said global images of surface to generate two or more registered images of surface; and integrating two or more said registered images of surface.

19. The method of claim 16, wherein said combining position and type of feature from two or more said computed images of surface comprises: estimating local defect properties from each of said computed images of surface; transforming local defect properties from two or more said computed images of surface to generate transformed local defect properties having a global coordinate system; and integrating said transformed local defect properties.

20. The method of claim 16, further comprising estimating the shape of said feature from said pixel region of feature.

* * * * *